US010639025B2

(12) United States Patent
Raybin et al.

(10) Patent No.: US 10,639,025 B2
(45) Date of Patent: May 5, 2020

(54) GRASPER NEEDLE CLOSURE DEVICE

(71) Applicant: BOSTON SCIENTIFIC SCIMED, INC., Maple Grove, MN (US)

(72) Inventors: Samuel Raybin, Marlborough, MA (US); Matthew B. Hollyer, Williamstown, VT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 156 days.

(21) Appl. No.: 15/629,438

(22) Filed: Jun. 21, 2017

(65) Prior Publication Data

US 2018/0028176 A1    Feb. 1, 2018

Related U.S. Application Data

(60) Provisional application No. 62/369,320, filed on Aug. 1, 2016.

(51) Int. Cl.
*A61B 17/04* (2006.01)
*A61B 17/00* (2006.01)
*A61B 17/06* (2006.01)

(52) U.S. Cl.
CPC ...... *A61B 17/0401* (2013.01); *A61B 17/0057* (2013.01); *A61B 17/0487* (2013.01); *A61B 2017/00663* (2013.01); *A61B 2017/0409* (2013.01); *A61B 2017/0417* (2013.01); *A61B 2017/0462* (2013.01); *A61B 2017/0464* (2013.01); *A61B 2017/061* (2013.01); *A61B 2017/06176* (2013.01)

(58) Field of Classification Search
CPC ............ A61B 17/0487; A61B 17/0401; A61B 2017/0409; A61B 2017/0417; A61B 2017/2926; A61B 2017/2945; A61B 17/062; A61B 17/29; A61B 17/0469
See application file for complete search history.

(56) References Cited

U.S. PATENT DOCUMENTS

2003/0149447 A1* 8/2003 Morency .......... A61B 17/06166
606/228
2004/0122473 A1* 6/2004 Ewers .............. A61B 17/00234
606/222

(Continued)

*Primary Examiner* — Diane D Yabut
*Assistant Examiner* — Majid Jamialahmadi
(74) *Attorney, Agent, or Firm* — Fay Kaplun & Marcin, LLP (57) ABSTRACT

A device for treating a tissue defect including a grasper including a pair of arms movable between a tissue receiving configuration and a tissue gripping configuration, a needle extending longitudinally from a proximal end to a distal end and including a first lumen extending longitudinally therethrough, the needle slidably received between the arms so that the needle is movable between a non-extended configuration, in which the distal end of the needle is proximal the distal ends of the arms, and an extended configuration, in which the distal end of the needle is distal of the distal end of the arms, and a first suture element slidably housed within the first channel and deployable therefrom to be anchored in a first target tissue into which it is inserted, the first suture element including a first cross member attached to a distal end of a first suture.

14 Claims, 9 Drawing Sheets

(56) References Cited

U.S. PATENT DOCUMENTS

2006/0264699 A1* 11/2006 Gertner ................ G06F 17/277
  600/37
2009/0312602 A1* 12/2009 Sakamoto .......... A61B 17/0401
  600/104
2010/0036395 A1* 2/2010 Miller ................ A61B 17/0401
  606/139
2015/0374358 A1* 12/2015 Suzuki ............... A61B 17/0401
  606/145

* cited by examiner

GRASPER NEEDLE CLOSURE DEVICE

PRIORITY CLAIM

The present disclosure claims priority to U.S. Provisional Patent Application Ser. No. 62/369,320 filed Aug. 1, 2016; the disclosure of which is incorporated herewith by reference.

BACKGROUND

Physicians have become more willing to perform more aggressive interventional and therapeutic endoscopic procedures including, for example, removal of larger lesions (e.g., cancerous masses), tunneling under mucosal layers in the gastro-intestinal (GI) tract to treat tissues below the mucosa, full thickness removal of tissue, inserting devices through the GI tract and then penetrating the GI organ to treat tissue outside the GI tract, and endoscopic treatment/repair of post-surgical issues (e.g., post-surgical leaks, breakdown of surgical staple lines, anastomotic leaks). These procedures may increase the risk of perforating the wall of the GI tract, or may require closure of the GI tract wall as part of the procedure. Endoscopic closure reduces cost and may reduce the trauma and inconvenience associated with these procedures. However, conventional tissue closure devices may be insufficient to close certain perforations.

SUMMARY

The present disclosure relates to a device for treating a tissue defect, comprising a grasper including a pair of arms movable between a tissue receiving configuration, in which distal ends thereof are separated from one another to receive tissue therebetween, and a tissue gripping configuration, in which the distal ends thereof are moved toward one another to grip tissue therebetween, a needle extending longitudinally from a proximal end to a distal end and including a first lumen extending longitudinally therethrough, the needle slidably received between the arms so that the needle is movable between a non-extended configuration, in which the distal end of the needle is proximal the distal ends of the arms, and an extended configuration, in which the distal end of the needle is distal of the distal end of the arms, and a first suture element slidably housed within the first channel and deployable therefrom to be anchored in a first target tissue into which it is inserted, the first suture element including a first cross member attached to a distal end of a first suture.

In an embodiment, the grasper may further include an inner sleeve extending from a proximal end to a distal end and including a channel extending therethrough, proximal ends of the arms connected to the distal end of the inner sleeve on opposing sides thereof.

In an embodiment, the arms may be biased toward the tissue receiving configuration.

In an embodiment, the grasper may further include an outer sleeve extending from a proximal end to a distal end and including a channel extending therethrough, the arms slidably movable relative to the outer sleeve to be moved between the tissue receiving configuration and the tissue gripping configuration, an interior surface of the outer sleeve constraining the arms toward the tissue gripping configuration when the arms are drawn into the channel of the outer sleeve.

In an embodiment, the device may further comprise a second suture element, the second suture element including a second cross member attached to a distal end of a second suture.

In an embodiment, the device may further comprise a cinch slidable along a length of the first and second sutures to move the first and second cross members toward one another and approximate the first and second target.

In an embodiment, at least one of the first and second sutures may include one of teeth and barbs along a length thereof.

In an embodiment, another one of the first and second sutures may include an opening for engaging one of the teeth and barbs.

In an embodiment, the needle may further comprise a second lumen extending longitudinally therethrough, the second suture element received within the second lumen of the needle.

In an embodiment, one of the first and second lumens may be open to an exterior of the needle along a length thereof.

In an embodiment, the first suture element may be movable between an insertion configuration, in which the first cross member is substantially aligned along a length of the first suture, and an anchoring configuration, in which first cross member extends transverse to a length of the first suture.

In an embodiment, the distal ends of the grasper may include distal tips extending laterally inward toward one another to grip the target tissue therebetween.

In an embodiment, the distal ends of the graspers may include a gripping structure which, when the arms are in the tissue gripping configuration, form an opening extending therethrough so that the needle, in the extended configuration, passes through the opening.

In an embodiment, gripping edges of the distal ends of the arms may include one of teeth, spikes and protrusions for gripping the target tissue received between the distal ends of the arms.

The present disclosure also relates to a device for approximating edges of a tissue defect, comprising a grasper including a pair of arms movable between a tissue receiving configuration, in which distal ends thereof are separated from one another to receive a target tissue therebetween, and a tissue gripping configuration, in which the distal ends thereof are moved toward one another to grip the target tissue therebetween, proximal ends of the arms coupled to a control member slidably received within an outer sleeve so that movement of the control member relative to the outer sleeve moves the arms between the tissue receiving configuration and the tissue gripping configuration. The device also comprises a needle extending longitudinally from a proximal end to a distal end and including a first lumen extending longitudinally therethrough, the needle slidably received between the arms so that the needle is movable between a non-extended configuration, in which the distal end of the needle is proximal the distal ends of the arms, and an extended configuration, in which the distal end of the needle is distal of the distal end of the arms, a first suture element slidably received in the first lumen and deployable therefrom, the first suture element including a first cross member attached to distal end of a first suture, and a second suture element slidably received within the needle and deployable therefrom, the second suture element including a second cross member attached to a distal end of a second suture, wherein the first cross member is insertable into a first target tissue and the second cross member is insertable into a second target tissue so that coupling and tightening the first and second sutures to move the first and second cross members toward one another to approximate the first and second target tissue.

The present disclosure also relates to a method for treating a target tissue, comprising inserting a device to a target site in a living body, the device including a grasper including a pair of arms movable between a tissue receiving configuration and a tissue gripping configuration and a needle slidably received between the arms, moving the arms from the tissue receiving configuration to the tissue gripping configuration so that a first target tissue along a first side of a tissue defect is received between distal ends of the arms is gripped therebetween, sliding the needle distally with respect to the grasper, to an extended configuration, so that the distal end of the needle pierces the first target tissue gripped by the arms of the grasper, deploying a first suture element from the needle so that a first cross member of the first suture element is anchored in the first target tissue and a first suture of the first suture element extends proximally therefrom, moving the arms from the tissue receiving configuration to the tissue gripping configuration so that a second target tissue along a second side of the tissue defect is received between distal ends of the arms is gripped therebetween, and deploying a second suture element from the needle so that a second cross member of the second suture element is anchored in the second target tissue and a second suture of the second suture element extends proximally therefrom, and coupling and tightening the first and second sutures so that the first and second cross members are moved toward one another.

BRIEF DESCRIPTION

DETAILED DESCRIPTION

The present disclosure may be further understood with reference to the following description and the appended drawings, wherein like elements are referred to with the same reference numerals. The present disclosure relates to devices for treating tissue and, in particular, relates to a tissue approximation and closure device. Exemplary embodiments of the present disclosure describe a tissue approximation and closure device comprising a grasper for grasping a target tissue and a needle extendable between arms of the grasper to pass suture t-tags through the target tissue grasped by the grasper. First and second portions of the suture T-tag may be inserted through first and second target portions of tissue, respectively, along opposing sides of a tissue defect, to approximate and close the tissue defect. It should be noted that the terms "proximal" and "distal" as used herein, are intended to refer to a direction toward (proximal) and away from (distal) a user of the device.

Figure 7:
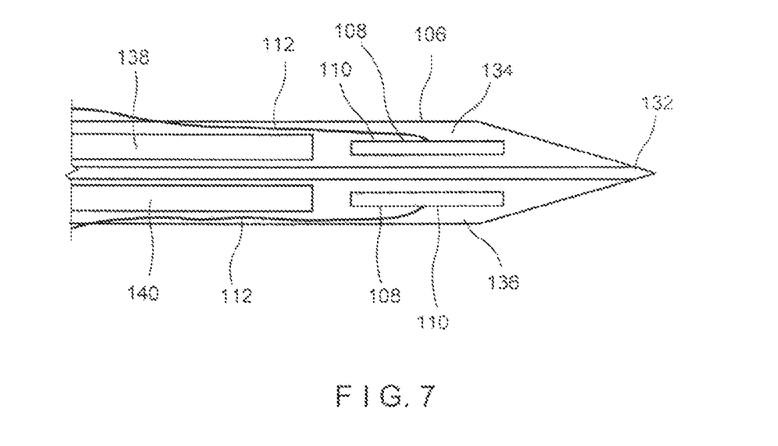
FIG. 7 shows a longitudinal cross-sectional view of the needle according to the device of FIG. 1.

As shown in FIGS. 1-10, a tissue approximation and closure device 100 according to an exemplary embodiment of the present disclosure comprises a grasper 102 including a pair of arms 104, movable between a tissue receiving configuration and a tissue gripping configuration, and a needle 106 slidably received between the arms 104 of the grasper 102 so that the needle 106 may be inserted into target tissue gripped by the grasper 102. A plurality of T-tag sutures 108 is slidably housed within the needle 106 so that the T-tag sutures 108 may be passed into the target tissue via the needle 106 as will be described in more detail below. Each T-tag suture 108 according to this embodiment includes a cross member 110 coupled to a length of suture 112 (FIG. 7). In use, the grasper 102 is first used to grip a first portion of target tissue along a first side of a tissue defect. The needle 106 may then be advanced distally to penetrate the gripped tissue. When the needle 106 is positioned as desired with the needle 106 extending through the gripped tissue so that a distal tip thereof is on a distal side of the gripped tissue, a first T-tag suture 108 is then pushed out of the needle 106 to force the cross member 110 thereof into the first portion of target tissue with the suture 112 extending out of the first portion of target tissue on a proximal side of the tissue defect. After insertion of the first T-tag suture 108 into the first portion of target tissue, the needle 106 is retracted and the grasper 102 is opened to release the tissue. The grasper 102 is then repositioned to grip a second portion of target tissue, e.g., a portion along a second side of the tissue defect. When the grasper 102 has gripped the second portion of target tissue as desired, the needle 106 is again advanced distally to pass through the second portion of target tissue and a second T-tag suture 108 is pushed out of the needle 106 to lodge the cross member 110 thereof in the second portion of target tissue with its length of suture 112 extending through the second portion of target tissue on the proximal side of the tissue defect. The lengths of suture 112 attached to the first and second T-tag sutures 108 are then cinched or tied to one another and tightened as desired in any other known manner to draw the first and second portions of target tissue into contact with one another to close the tissue defect. The grasper 102 may then be opened to release the second portion of target tissue and additional T-tag sutures 108 may be placed in a similar manner to more fully close the tissue defect and/or to close additional tissue defects as would be understood by those skilled in the art.

As would be understood by those skilled in the art, the grasper 102 and the needle 106 are coupled to a proximal portion (not shown) of the device 100 including, for example, a flexible member and a handle member facilitating the insertion of the grasper 102 and needle 106 to a target site within a living body. For example, the proximal portion may comprise a flexible sheath that houses the needle 106 and one or more control members for operating the grasper 102 so that the device 100 may be inserted through a working channel of an endoscope to target sites in the body. The handle member may include any known actuating mechanisms for actuating arms 104 of the grasper 102, for moving the needle 106 and for deploying the T-tag suture 108, as will be described in further detail below.

Figure 1:
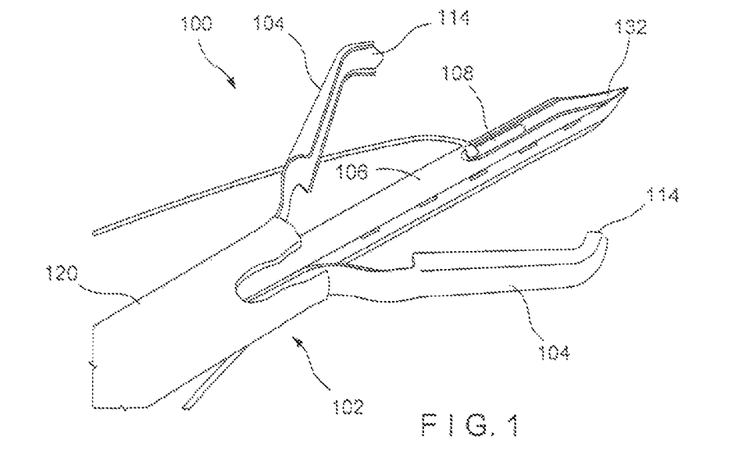
FIG. 1 shows a perspective view of a device according to an exemplary embodiment of the present invention.
Figure 2:
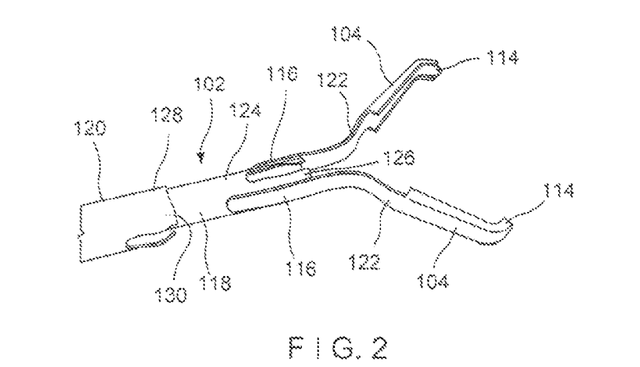
FIG. 2 shows a perspective view of a grasper according to the device of FIG. 1, in a tissue receiving configuration.
Figure 3:
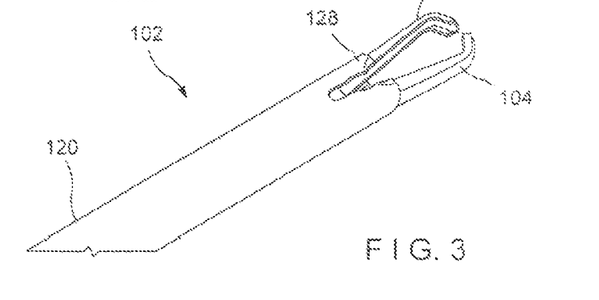
FIG. 3 shows a perspective view of the grasper according to the device of FIG. 1, in a tissue gripping configuration.

The grasper 102, as shown in FIGS. 2-3, comprises the pair of arms 104, proximal ends 116 of which are connected to one another via an inner sleeve 118 slidably received within an outer sleeve 120. The inner sleeve 118 extends from a proximal end (not shown) to a distal end 124 and includes a channel 126 extending therethrough. Proximal ends 116 of the arms 104 are connected to the distal end 124 of the inner sleeve 118 so that the arms 104 extend distally from opposing sides of the inner sleeve 118. The inner sleeve 118 may be substantially tubular. Similarly, the outer sleeve 120 extends from a proximal end (not shown) to a distal end 128 and includes a channel 130 extending therethrough. The channel 130 of the outer sleeve 120 is sized and shaped to slidably receive the inner sleeve 118 therein. Thus, the inner and outer sleeves 118, 120 may be slid longitudinally relative to one another to move the grasper 102 between the tissue receiving configuration, as shown in FIG. 2, and the tissue gripping configuration, as shown in FIG. 3. As would be understood by those skilled in the art, although the inner and outer sleeves 118, 120 are described and shown as being substantially tubular, the inner and outer sleeves 118, 120 may have any of a variety of shapes so long as the inner and outer sleeves 118, 120 are coupled to be longitudinally movable relative to one another.

In one embodiment, the pair of arms 104 is biased toward the tissue receiving configuration, in which distal ends 114 thereof are separated from one another to receive target tissue therebetween, so that, when the inner sleeve 118 is moved proximally relative to the outer sleeve 120 drawing portions of the arms 104 into the sleeve 120, an interior surface of the outer sleeve 120 contacts the arms 104 and draws them radially inward toward one another (i.e., toward the tissue gripping configuration). Each of the arms 104 extends from its proximal end 116 to its distal end 114 and is sized and shaped so that, when a proximal part of the arm 104 comes into contact with the interior surface of the outer sleeve 120, the arm 104 is urged toward the tissue gripping configuration. In particular, each of the arms 104 in this embodiment includes a shoulder 122 shaped so that, when the inner sleeve 118 is drawn proximally into the outer sleeve 120, an interior surface of the outer sleeve 120 engages an exterior surface of the shoulder 122 of each of the arms 104, drawing the arms 104 together toward the tissue gripping configuration. When the inner sleeve 118 is moved distally relative to the outer sleeve 120, the shoulder 122 extends distally beyond a distal end of the outer sleeve 120 extending the arms 104 out of the outer sleeve permitting the arms 104 to move apart according to their natural bias toward the tissue receiving configuration. The distal end 114 of each of the arms 104 in this embodiment extends laterally inward toward the distal end 114 of the other of the arms 104 to facilitate gripping of the target tissue. However, as would be understood by those skilled in the art, the distal end 114 may take any of a variety of shapes and may include any of a variety of gripping structures such as, for example, teeth, spikes, and/or other protrusions.

In yet another embodiment, not shown, the arms 104 may be moved between the tissue receiving and the tissue gripping configurations via a pull wire connected thereto. For example, the proximal ends 116 of the arms 104 may be pivotally coupled to the distal end 124 of the inner sleeve 118 with a distal end of the pull wire coupled to each of the arms 104 distally of this pivotal connection so that drawing the pull wire proximally relative to the inner sleeve 118 moves the arms 104 from the tissue receiving configuration to the tissue gripping configurations with distal movement of the pull wire relative to the inner sleeve 118 moving the arms 104 from the tissue gripping configuration to the tissue receiving configuration. It will be understood by those of skill in the art that, in this embodiment, an outer sleeve 120 is not required.

Figure 11:
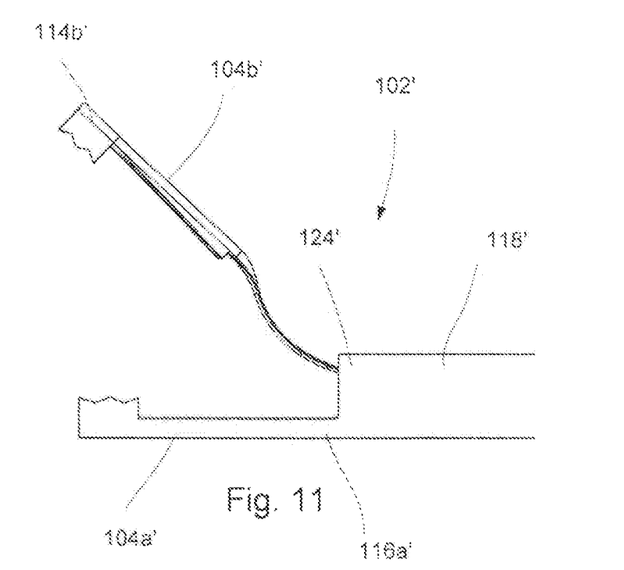
FIG. 11 shows a longitudinal side view of a grasper according to another exemplary embodiment of the present disclosure.
Figure 12:
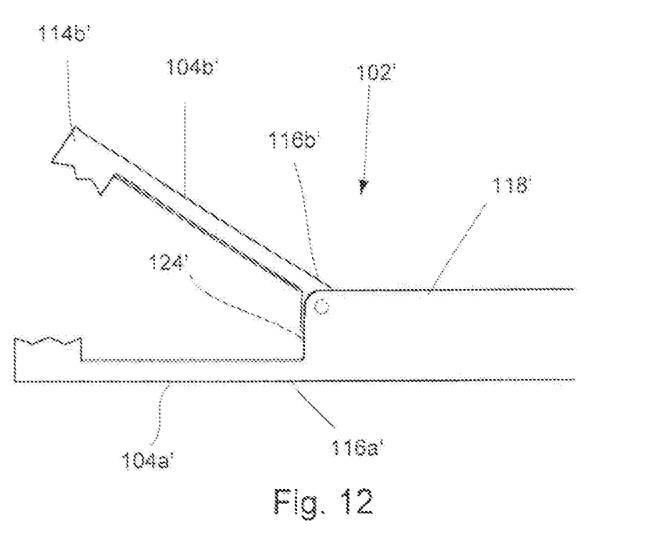
FIG. 12 shows a longitudinal side view of a grasper according to an alternate embodiment of the present disclosure.

Although the above embodiments describe and show both of the arms 104 as being movable between the tissue receiving configuration and the tissue gripping configuration, in another embodiment, as shown in FIGS. 11-12, a first one of the arms 104a' of a grasper 102' is rigidly fixed at a proximal end 116a' thereof to a distal end 124' of an inner sleeve 118' while a second one of the arms 104b' is movable relative to the inner sleeve 118'. The first one of the arms 104a' may extend along an axis substantially parallel to a longitudinal axis of the inner sleeve 118'. The second one of the arms 104b' may be movably connected to the inner sleeve 118' to move the grasper 102' between a tissue receiving configuration, in which a distal end 114b' thereof extends away from the first one of the arms 104a', and a tissue gripping configuration, in which the distal end 114b' is moved toward the first one of the arms 104a'. In one example, as shown in FIG. 11, the second one of the arms 104b' may be longitudinally movable with respect to the inner sleeve 118' to move the grasper 102' between the tissue receiving and gripping configurations. Specifically, the second one of the arms 104b' may be biased toward the tissue receiving configuration so that the second one of the arms 104b' may be drawn into the inner sleeve 118' to move the grasper 102' toward the tissue gripping configuration. In this embodiment, an outer sleeve is not necessary. In another example, as shown in FIG. 12, the second one of the arms 104b' may be connected to the inner sleeve at a proximal end 116b' thereof via, for example, a pivotal connection. In this embodiment, an outer sleeve substantially similar to the outer sleeve 120 described above may be slidable over the inner sleeve 118' to move the grasper 102' between the tissue receiving and the tissue gripping configuration. The grasper 102' may be used in a manner substantially similar to the clip 102.

Figure 4:
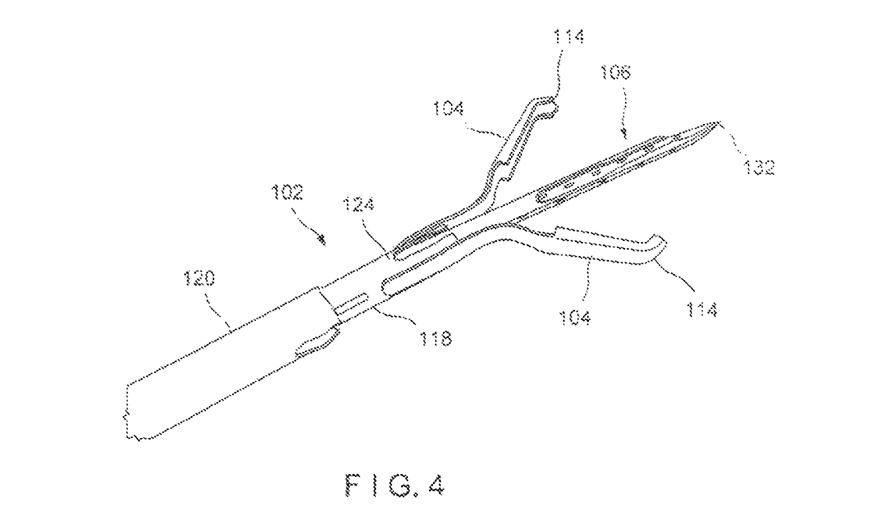
FIG. 4 shows a perspective view of a needle extending through the grasper according to the device of FIG. 1, the grasper in the tissue receiving configuration.
Figure 5:
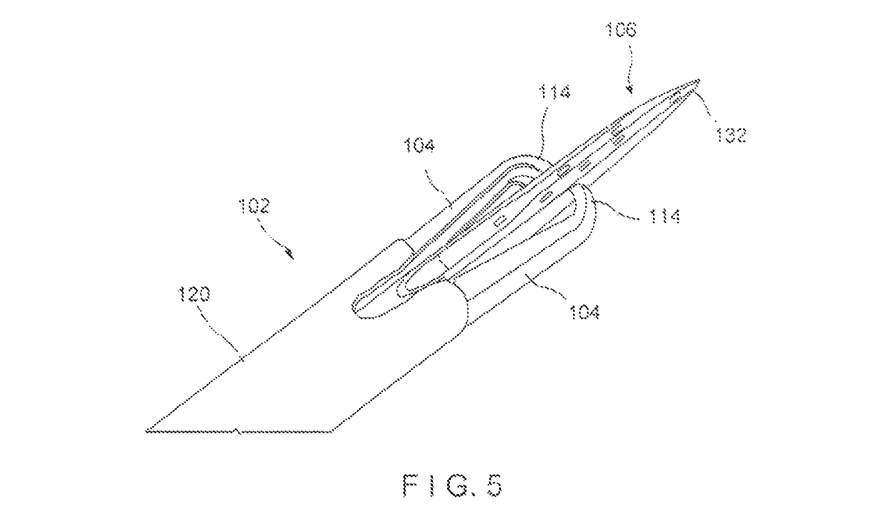
FIG. 5 shows a perspective view of the needle extending through the grasper according to the device of FIG. 1, the grasper in the tissue gripping configuration.
Figure 6:
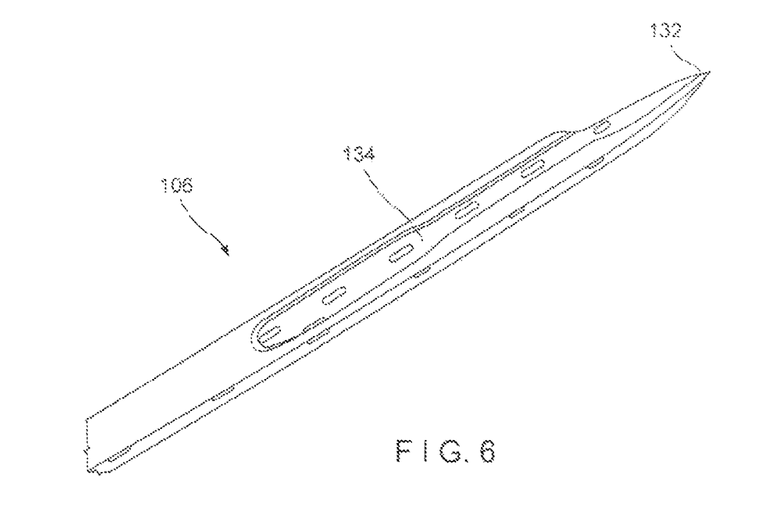
FIG. 6 shows a perspective view of the needle according to the device of FIG. 1.

As shown in FIGS. 4-7, the needle 106 is coaxially received within the channel 126 (FIG. 2) of the inner sleeve 118 and is slidable therein between an extended configuration and a non-extended configuration. The needle 106 extends longitudinally from a proximal end to a distal end 132. In the extended configuration, the distal end 132 of the needle 106 extends distally beyond the distal end 124 of the inner sleeve 118 to pierce target tissue gripped between the distal ends 114 of the arms 104. In the non-extended configuration, the needle 106 is withdrawn proximally with respect to the inner sleeve 118 so that the distal end 132 of the needle 106 is housed in the channel 126. The needle 106 may be moved between the extended and non-extended configurations when, as shown in FIG. 4, the grasper 102 is in the tissue receiving configuration, and when, as shown in FIG. 5, the grasper 102 is in the tissue gripping configuration. The distal end 132 of the needle 106 may be sharpened or tapered to facilitate insertion of the needle 106 into target tissue as would be understood by those skilled in the art.

In one embodiment, as shown in FIG. 7, the needle 106 may be a dual-slotted needle including a first lumen 134 and a second lumen 136 extending longitudinally therethrough. The first and/or second lumens 134, 136 may be open to an exterior of the needle 106 along a portion of a length thereof. The first and second lumens 134, 136, however, are not required to be open to the exterior of the needle 106, except at the distal end 132. The first lumen 134 may house a first plurality of T-tag sutures 108 while the second lumen 136 houses a second plurality of T-tag sutures 108. Each of the first and second lumens 134, 136 is open at the distal end 132 so that the cross members 110 of the first and second pluralities of T-tag sutures may be deployed therefrom as described above.

In particular, a first actuating element 138 is received within the first lumen 134 proximally of a first one of the cross members 110 and a second actuating element 140 is received within the second lumen 136 proximally of the second one of the cross members 110. Thus, when it is desired to insert one of the T-tag sutures 108, a corresponding one of the first and second actuating elements 138, 140 is moved distally with respect to the needle 106 to deploy the desired a T-tag suture 108 from one of the first and second pluralities thereof. The first and second actuating elements 138, 140 may be configured as rods or other longitudinal members suitable for pushing the cross members 110 and the corresponding sutures 112 from the first and second lumens 134, 136, respectively. Although only a single pair of T-tag sutures 108 is described, it will be understood by those of skill in the art that the needle 106 may be configured to house any number of T-tag suture's 108 in the first and second lumens 134, 136, respectively. In particular, each of the first and second lumens 134, 136, respectively, may house a plurality of cross members 110 in line therewithin with the respective suture lengths 112 trailing proximally therefrom.

In another embodiment, not shown, the needle 106 may include a single lumen with multiple T-tag sutures 108 contained in line therein. The T-tags 108, however, may be housed within the needle 106 in any of a variety of configurations, so long as each of the T-tag sutures 108 may be applied to treat tissue, as will be described in more detail below.

Figure 8:
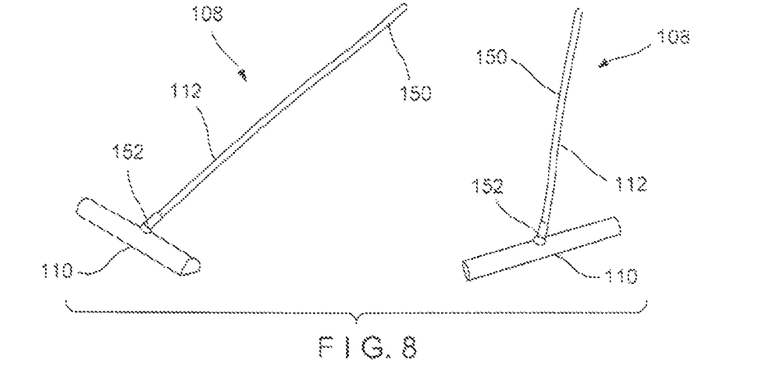
FIG. 8 shows a perspective view of a T-tag suture according to the device of FIG. 1.

As shown in FIG. 8, each of two T-Tag sutures 108 includes a cross member 110 and a length of suture 112. As described above, the sutures 112 of the two T-tag sutures 108 may be cinched, tied or otherwise coupled or connected to one another to approximate separated portions of tissue and/or to close a tissue defect. Specifically, each of the lengths of suture 112 extends from a proximal portion 150 to a distal end 152 attached to the cross member 110. The cross member 110 may be configured as an elongated element movably or rotatably connected to the distal end 152 of the suture 112 so that the cross member 110 is movable between an insertion configuration in which the cross member 110 is substantially parallel to the suture 112 and an anchoring configuration in which the cross member 110 is transverse to the suture 112 in, for example, a substantially T-shaped configuration.

The cross members 110 of the T-tag sutures 108 are housed within the first and second lumens 134, 136, respectively, of the needle 106 in the insertion configuration. Upon deployment from a respective one of the first and second lumens 134, 136 into target tissue, the cross members 110, are rotated to the T-shaped configuration anchoring the T-tag sutures 108 in the tissue into which they have been inserted. The cross members 110 may be biased toward the T-shaped configuration or may simply revert to this position when tension is applied to the corresponding suture 112 and contact with the surrounding tissue urges the cross members to extend transverse to the direction in which the tension is applied (i.e., along the suture 112).

Figure 13:
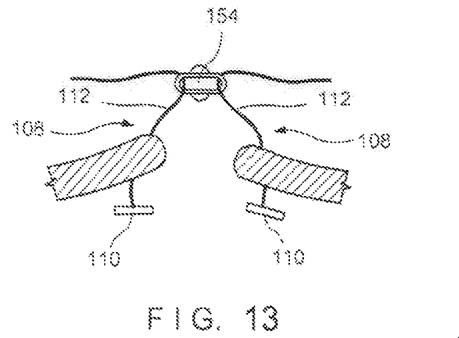
FIG. 13 shows a side view of the T-tag suture according to the device of FIG. 1.
Figure 14:
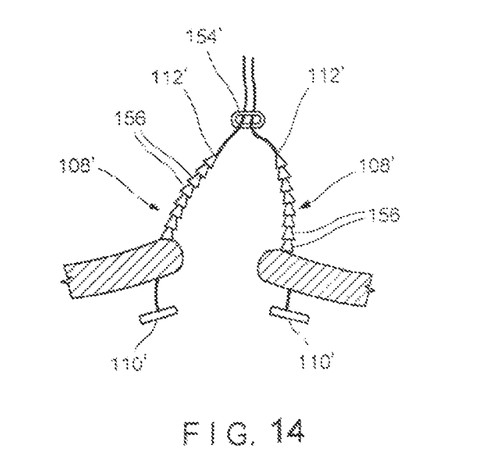
FIG. 14 shows a side view of a T-tag suture according to another embodiment of the present disclosure.

As shown in FIG. 13, T-tag sutures 108 of one exemplary embodiment may further include a cinching element 154 movable distally over its suture 112 to capture and couple to the suture 112 of another T-tag suture 108 to enable a user to draw the sutures of the two T-tag sutures 108 toward one another and to lock them in a desired position relative to one another thereby constraining the portions of tissue within which the respective cross members 110 are embedded to remain in a desired spatial relation relative to one another (e.g., held in contact with one another to seal a tissue defect). Once the cinching element 154 has been moved to a desired position along the sutures 112—i.e., a desired level of approximation has been achieved between the portions of target tissue—the cinching element 154 may be crushed or otherwise deformed to fix the cinching element 154 in the desired position along the sutures 112. In another example, as shown in FIG. 14, T-tag sutures 108' may be substantially similar to the T-tag sutures 108, comprising a cinching element 154'. Sutures 112' of the T-tag sutures 108', however, includes barbs 156' or teeth extending therealong to act as a ratchet so that the cinching element 154' may be moved therealong to a desired position as discussed above and so that the ratchet action between the cinching element 154' automatically locks the sutures 112' together as desired. Thus, the cinching element 154' is not required to be crushed or deformed to fix the cinching element 154' in a desired position along the sutures 112'.

Figure 15:
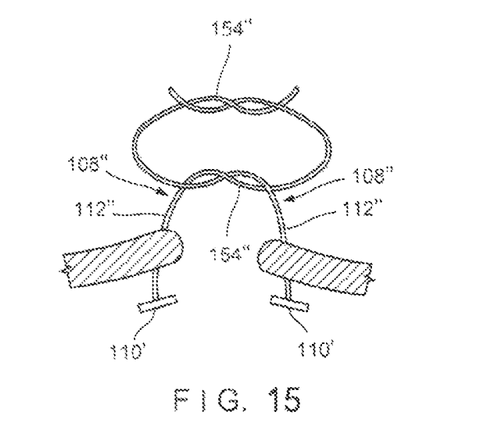
FIG. 15 shows a side view of a T-tag suture according to yet another embodiment of the present disclosure.

In another example, as shown in FIG. 15, T-tag sutures 108" are substantially similar to the T-tag sutures 108, 108', but do not require a cinching element. Rather, sutures 112" thereof may be knotted together to fix the cross members 110" thereof at a desired distance relative to one another. In one embodiment, a knot 154" may be tied by a user after the cross members 110" have been applied to the tissue as desired. In another embodiment, the knot 154" may be moved along the sutures 112" so that drawing proximal ends of the sutures 112" proximally pushes the knot 154" distally along the sutures 112" to draw the cross members 110" of the two T-tag sutures 108" toward one another.

Although the above embodiments show and describe identical T-tag sutures 108, 108', 108" applied to each of the first and second target tissues, it is also possible to insert different T-tag sutures into each of the first and second target tissues, so long as anchoring portions (e.g., cross members) of each of the T-tag sutures inserted into each of the first and second target tissue may be drawn toward one another to approximate the portions of tissue into which they are inserted.

Figure 16:
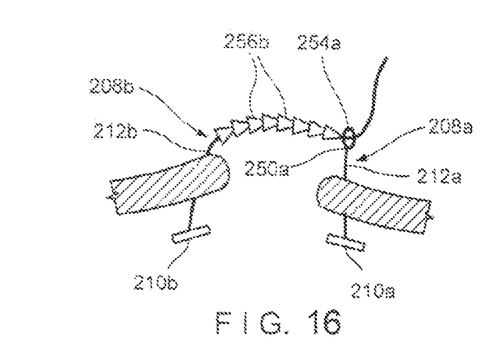
FIG. 16 shows a side view of a T-tag suture according to another exemplary embodiment of the present disclosure.
Figure 17:
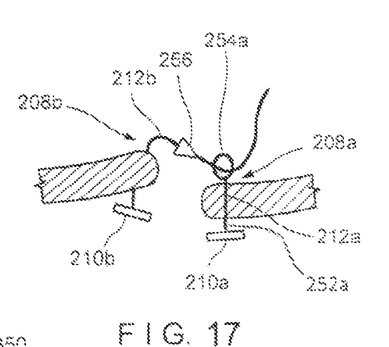
FIG. 17 shows a side view of a T-tag suture according to yet another embodiment of the present disclosure.

In one example, as shown in FIG. 16, a first T-tag suture 208a may be inserted into a first target tissue along a first side of a tissue defect while a second T-tag suture 208b may be inserted into a second target tissue along a second side of the tissue defect. The first T-tag suture 208a may be substantially similar to the T-tag sutures described above, comprising a cross member 210a at a distal end 252a of a suture 212a. A proximal end 250a of the suture 212a, however, includes a loop 254a or other opening through which a length of a suture 212b of the second T-tag suture 208b may be received. In particular, the second T-tag suture 208b may be substantially similar to the T-tag suture 108' described above, comprising a cross member 210b and a suture 212b, the suture 212b including barbs 256b or teeth extending along a length thereof. The length of the suture 212b is passed through the loop 254a so that, when the suture 212b of the second T-tag suture 208 is drawn proximally, the first and second anchor portions 210a, 210b of the first and second T-tag sutures 208a, 208b, respectively, are drawn toward one another. The barbs 256b engage the opening of the loop 254a, acting as a ratchet so that the suture 212b may be drawn proximally through the loop 254a, but is prevented from being moved distally therethrough. Thus, drawing the suture 212b approximates the first and second target tissue in which the cross members 210a, 210b of the first and second T-tag sutures 208a, 208b, respectively, are inserted, while also maintaining the desired level of approximation. The suture portion 212b may include multiple barbs 256b or teeth, as shown in FIG. 16, to allow the cross members 210a, 210b to be positioned at varying distances relative to one another, or, as shown in FIG. 17, may include a single barb 256b, tooth or other enlargement so that the cross members 210a, 210b may be fixed with respect to one another at a predetermined distance.

Figure 18:
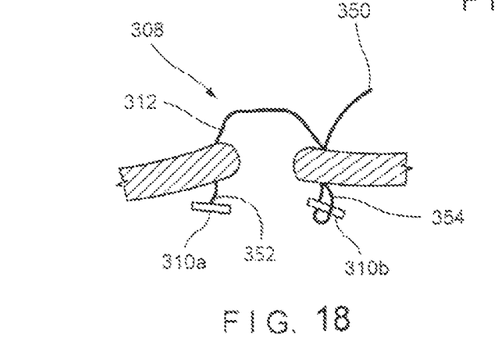
FIG. 18 shows a side view of a T-tag suture according to another embodiment of the present disclosure.
Figure 19:
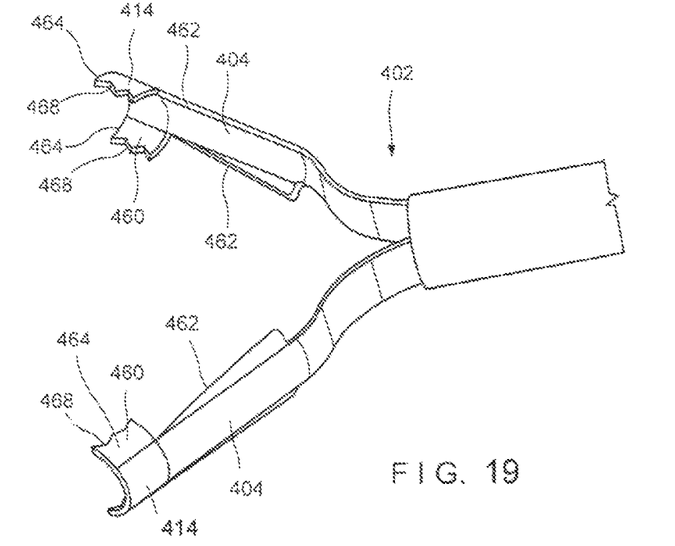
FIG. 19 shows a perspective view of a grasper according to another embodiment of the present disclosure.
Figure 20:
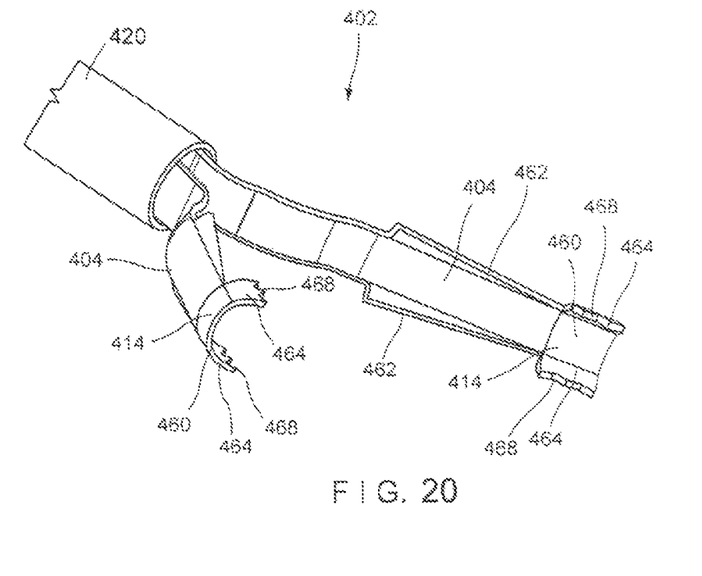
FIG. 20 shows another perspective view of the grasper according to FIG. 19.
Figure 21:
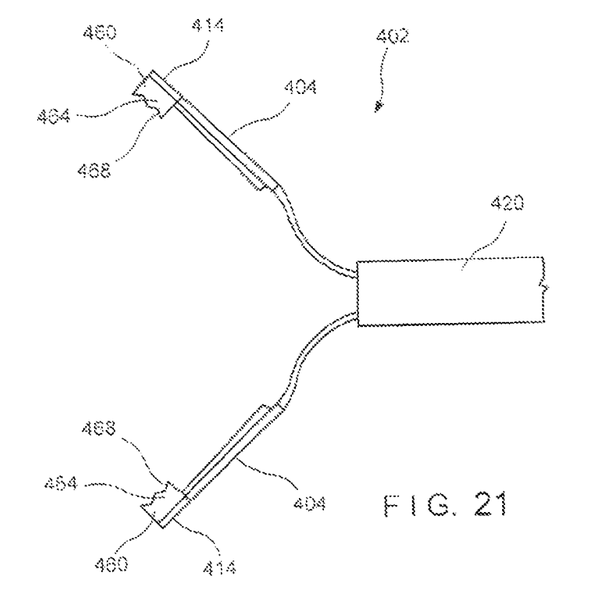
FIG. 21 shows a side view of the grasper according to FIG. 19, in an open tissue receiving configuration.
Figure 22:
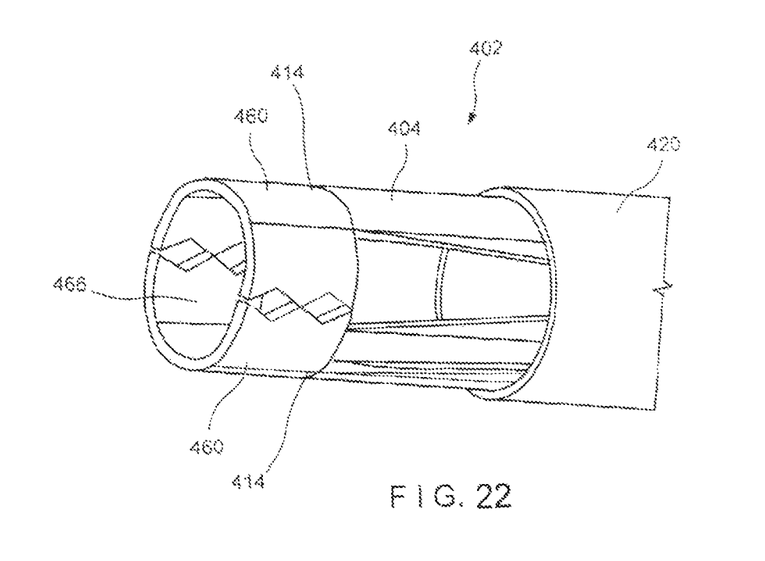
FIG. 22 shows a perspective view of the grasper according to FIG. 19, in a closed tissue gripping configuration.

In another example, as shown in FIG. 18, a T-tag suture 308 includes a first cross member 310a and a second cross member 310b connected to one another via a single length of suture 312. In particular, the first cross member 310a is connected to a first end 352 of the suture 312. The second cross member 310b includes a pair of holes extending laterally therethrough. The suture 312 is threaded through the pair of holes so that, in an anchoring configuration, the cross member 310b extends transverse to the suture 312 in a substantially T-shaped configuration. Thus, when the cross members 310a, 310b are inserted into first and second target tissues, respectively, drawing a second end 350 of the suture 312 proximally causes the suture 312 to slide through the pair of holes of the second cross member 310, shortening a length of suture 312 extending between the first and second cross members 310a, 310b. The first and second target tissues, in which the first and second cross members 310a, 310b are inserted, are thereby approximated. The T-tag suture 308 may also include a cinch 354 which extends about overlapping portions of the suture 312 so that, when the second cross-member 310b is inserted into the second target tissue, the cinch 354 extends on a proximal side of the second target tissue. Once a desired level of approximation has been achieved, the cinch 354 may be positioned against a proximal surface of the second target tissue and deformed or crushed to fix the cinch 354 in the desired position along the suture 312 to maintain the desired level of approximation. Alternatively, the cinch 354 may be configured so that the proximal end 350 of the suture 312 may be drawn proximally relative thereto, but is prevented from being moved distally relative thereto. For example, portions of a length of the suture 312 may include teeth, barbs or other protrusions for acting as a ratchet mechanism. In another example, a force required to slide the suture 312 through the cinch 354 may be greater than any tension along a portion of the suture 312 extending between the first and second cross-members 310a, 310b, when the first and second cross members 310a, 310b are used to approximate tissue.

The above described T-tag sutures are exemplary only. It will be understood by those of skill in the art that the device 100 may include any of a variety of suture mechanisms so long as the T-tag sutures include anchoring portions such as, for example, cross members, which may be anchored or inserted into portions of tissue so that the portions of tissue into which they have been anchored may be moved toward one another via the suture mechanism.

Figure 9:
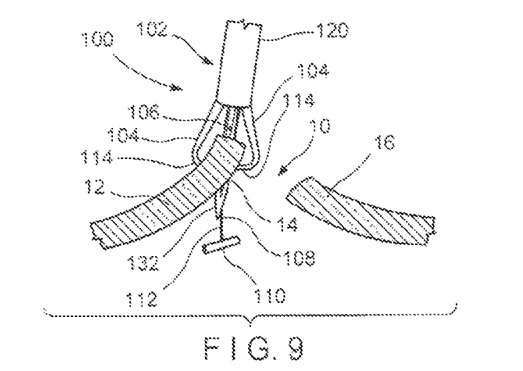
FIG. 9 shows a side view of the device according to FIG. 1, gripping and piercing a target tissue.

In use, a distal portion of the device 100, including the grasper 102 and the needle 106, may be inserted into a target site within a living body via, for example, a working channel of an endoscope. The device 100 may be inserted with the grasper 102 in a closed, tissue gripping configuration and the needle 106 in the non-extended configuration. Once the device 100 is at the target site, the grasper 102 may be opened from the tissue gripping configuration to the tissue receiving configuration so that a first target tissue 12 along a first side of a tissue defect 10 may be received between the arms 104 of the grasper 102. The grasper 102 may then be moved toward the tissue gripping configuration so that the first target tissue 12 is gripped by the distal ends 114 of the arms 104. As shown in FIG. 9, the needle 106 may then be moved distally relative to the grasper 102 toward the extended configuration so that the distal end 132 pierces the first target tissue 12, passing through the first target tissue 12 past a distal surface 14 thereof. The first one of the T-tag sutures 108 may then be deployed from the needle 106 by, for example, pushing the first actuating element 138 distally with respect to the first lumen 134. As the cross member 110 extends distally past the distal end 132 of the needle 106, the cross member 110 is moved from the insertion configuration toward the T-shaped anchoring configuration. Thus, when the grasper 102 is moved toward the tissue receiving configuration to release the first target tissue 12 and the needle 106 is withdrawn therefrom toward the non-extended configuration, the first of the T-tag sutures 108 remains anchored to the first target tissue 12.

Figure 10:
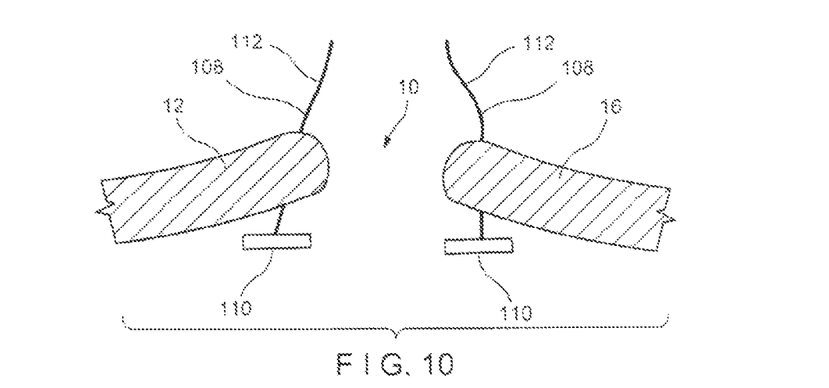
FIG. 10 shows a side view of the T-tag suture according to the device of FIG. 1, anchored in the target tissue.

The grasper 102 may then be moved toward a second target tissue 16 along a second side of the tissue defect and positioned so that the second target tissue is received between the arms 104. The first and second target tissue 12, 16 may extend along opposing sides of the tissue defect 10. The arms 104 are then moved toward the tissue gripping configuration so that the second target tissue 16 is gripped between the distal ends 114 thereof. Similarly to the first target tissue 12, the needle 106 may then be moved from the non-extended configuration toward the extended configuration so that the distal end 132 of the needle 106 pierces the second target tissue 16. A second one of the T-tag sutures 108 may then be applied to the second target tissue 16, the cross member 110 being moved toward the T-shaped anchoring configuration as it is released from the needle 106, as shown in FIG. 10. Thus, the second of the T-tag sutures 108 remains anchored to the second target tissue 16 even when the grasper 102 is opened to release the second target tissue and the needle 106 is withdrawn toward the non-extended configuration. Once the T-tag sutures 108 have been applied to the first and second target tissue, sutures 112 of each of the T-tag sutures 108 are drawn toward one another by, for example, cinching, knotting or any other coupling mechanism. The cinching, knotting and/or coupling of the sutures 112 approximates the first and second portions of target tissue 12, 16 and also maintains the tissue defect 10 in this closed configuration.

Although the method above describes the deployment of one pair of T-tag sutures 108, as described above, the needle 106 of the device 100 may house a plurality of pairs of T-tag sutures 108. Thus, additional pairs of T-tag sutures 108 may be applied, without having to remove the device 100 to reload the device 100 with additional T-tag sutures 108, as desired or necessary. For example, additional T-tag sutures 108 may be applied along a length of the tissue defect until the entire tissue defect is closed.

As shown in FIGS. 19-22, a grasper 402 according to another exemplary embodiment may be utilized in the device 100 in a manner substantially similar to the grasper 102. Similarly to the grasper 102, the grasper 402 includes arms 404 which may be coupled to a distal end of an inner sleeve (not shown). The arms 404 may be moved between an open tissue receiving configuration and a closed tissue gripping configuration by, for example, moving an outer sleeve 420 longitudinally with respect to the inner sleeve. Distal ends 414 of each of the arms 104, however, include a gripping element 460 which, when the arms 404 are moved toward the tissue gripping configuration, form an opening 466 through which the needle 106 may be extended. For example, each gripping element 460 may include protrusions 464 extending laterally inward from opposing longitudinal edges 462 of each arm 404. In one embodiment, the protrusions 464 may be curved to form a substantially semi-circular gripping element 460 so that, when the arms 404 are moved toward the tissue gripping configuration, the gripping elements 460 of the arms 404 may together form a substantially cylindrical shape. Thus, when the needle 106 is moved toward the extended configuration, the needle 106 extends between the distal ends 414, through the opening 466 of the cylinder formed via the gripping elements 460. Gripping edges 468 of each of the gripping elements 460 may include teeth, spikes, or other similar gripping structures for enhancing the grip of target tissue between the distal ends 414.

It will be apparent to those skilled in the art that various modifications may be made in the present disclosure, without departing from the scope of the disclosure.

What is claimed is:

1. A device for treating a tissue defect, comprising:
a grasper including a pair of arms movable between a tissue receiving configuration, in which distal ends thereof are separated from one another to receive tissue therebetween, and a tissue gripping configuration, in which the distal ends thereof are moved toward one another to grip tissue therebetween, each of the arms including a shoulder adjacent to a proximal end thereof;
a needle extending longitudinally from a proximal end to a distal end and including a first lumen extending longitudinally therethrough, the needle slidably received between the arms so that the needle is movable between a non-extended configuration, in which the distal end of the needle is proximal to the distal ends of the arms, and an extended configuration, in which the distal end of the needle is distal of the distal end of the arms; and
a first suture element slidably housed within the first lumen and deployable therefrom to be anchored in a first target tissue into which the first suture element is inserted, the first suture element including a first cross member attached to a distal end of a first suture,
wherein the grasper further includes an inner sleeve extending from a proximal end to a distal end and including a channel extending therethrough, the proximal ends of the arms are connected to the distal end of the inner sleeve on opposing sides thereof,
wherein, when the inner sleeve moves proximally, the arms move toward the tissue gripping configuration, and
wherein the grasper further includes an outer sleeve slidably receiving the inner sleeve and extending from a proximal end to a distal end, the outer sleeve including a channel extending therethrough, each of the shoulders of the arms being shaped so that, as the inner sleeve is drawn proximally into the outer sleeve, an interior surface of the outer sleeve engages an exterior surface of each of the shoulders, drawing the arms together toward the tissue gripping configuration.

2. The device of claim 1, wherein the arms are biased toward the tissue receiving configuration.

3. The device of claim 1, further comprising a second suture element to be anchored in a second target tissue, the second suture element including a second cross member attached to a distal end of a second suture.

4. The device of claim 3, further comprising a cinch slidable along a length of the first and second sutures to move the first and second cross members toward one another and approximate the first target tissue and the second target tissue.

5. The device of claim 3, wherein at least one of the first and second sutures includes one of teeth and barbs along a length thereof.

6. The device of claim 5, wherein another one of the first and second sutures includes an opening for engaging one of the teeth and barbs.

7. The device of claim 3, wherein the needle further comprises a second lumen extending longitudinally therethrough, the second suture element received within the second lumen of the needle.

8. The device of claim 7, wherein one of the first and second lumens are open to an exterior of the needle along a length thereof.

9. The device of claim 1, wherein the first suture element is movable between an insertion configuration, in which the first cross member is substantially aligned along a length of the first suture, and an anchoring configuration, in which first cross member extends transverse to the length of the first suture.

10. The device of claim 1, wherein the distal ends of the grasper arms include distal tips extending laterally inward toward one another to grip tissue therebetween.

11. The device of claim 1, wherein the distal ends of the grasper arms include a gripping structure which, when the arms are in the tissue gripping configuration, form an opening extending therethrough so that the needle, in the extended configuration, passes through the opening.

12. The device of claim 1, wherein gripping edges of the distal ends of the arms include one of teeth, spikes and protrusions for gripping tissue received between the distal ends of the arms.

13. The device of claim 1, wherein the arms move into the tissue receiving configuration upon moving distally away from the outer sleeve.

14. A device for approximating edges of a tissue defect, comprising:
a grasper including a pair of arms movable between a tissue receiving configuration, in which distal ends thereof are separated from one another to receive a target tissue therebetween, and a tissue gripping configuration, in which the distal ends thereof are moved toward one another to grip the target tissue therebetween, each of the arms including a shoulder adjacent to a proximal end thereof, the proximal ends of the arms coupled to an inner sleeve slidably received within an outer sleeve so that movement of the inner sleeve relative to the outer sleeve moves the arms between the tissue receiving configuration and the tissue gripping configuration;

a needle extending longitudinally from a proximal end to a distal end and including a first lumen extending longitudinally therethrough, the needle slidably received between the arms so that the needle is movable between a non-extended configuration, in which the distal end of the needle is proximal to the distal ends of the arms, and an extended configuration, in which the distal end of the needle is distal of the distal end of the arms;

a first suture element slidably received in the first lumen and deployable therefrom, the first suture element including a first cross member attached to a distal end of a first suture; and a second suture element slidably received within the needle and deployable therefrom, the second suture element including a second cross member attached to a distal end of a second suture, wherein the first cross member is insertable into a first target tissue and the second cross member is insertable into a second target tissue so that coupling and tightening of the first and second sutures will move the first and second cross members toward one another to approximate the first and second target tissue, wherein the outer sleeve slidably receiving the inner sleeve and extending from a proximal end to a distal end, the outer sleeve including a channel extending therethrough, each of the shoulders of the arms being shaped so that, as the inner sleeve is drawn proximally into the outer sleeve, an interior surface of the outer sleeve engages an exterior surface of each of the shoulders, drawing the arms together toward the tissue gripping configuration.

* * * * *